United States Patent [19]

Omicioli

[11] Patent Number: 4,702,233

[45] Date of Patent: Oct. 27, 1987

[54] VENTILATED NECK BRACE AND RELATED STRUCTURES

[76] Inventor: Florio F. Omicioli, 205 Elm St., Apt. 2, West Haven, Conn. 06516

[21] Appl. No.: 841,206

[22] Filed: Mar. 19, 1986

[51] Int. Cl.$^4$ .......................... A61H 7/00; A61F 5/01
[52] U.S. Cl. ............................... 128/75; 128/DIG. 23
[58] Field of Search ...................... 128/76 R, 75, 87 B, 128/DIG. 23

[56] References Cited

U.S. PATENT DOCUMENTS

| | | | |
|---|---|---|---|
| 2,065,191 | 12/1936 | Loeber | 128/62 R |
| 2,210,858 | 8/1940 | Loeber | 128/62 R |
| 2,825,328 | 3/1958 | Olsen | 128/76 R |
| 3,008,464 | 11/1961 | Atkins | 128/DIG. 23 |
| 4,325,363 | 4/1982 | Berkeley | 128/75 |
| 4,538,597 | 9/1985 | Lerman | 128/75 |

FOREIGN PATENT DOCUMENTS 987981  4/1976  Canada .................................. 128/75

*Primary Examiner*—Edgar S. Burr
*Assistant Examiner*—Tonya Lamb
*Attorney, Agent, or Firm*—DeLio & Associates

[57] ABSTRACT

An improved ventilated body or neck brace for effective removal of body heat and moisture from inside the brace utilizing a plurality of vent holes in combination with a network of air distributing channels on the inside surface of the brace.

10 Claims, 3 Drawing Figures

VENTILATED NECK BRACE AND RELATED STRUCTURES

BACKGROUND OF THE INVENTION

The present invention relates to adjustable body and neck braces for encircling a portion of the body and immobilizing that portion and, more particularly, to a brace having improved interior air circulation and ventilation.

For example, neck braces or cervical collars are commonly employed for treating neck injuries such as whiplash and other dislocations which result in muscular strain or nerve pressure in the cervical region. These braces substantially immobilize the wearer's head while, at the same time, providing a means for supporting the wearer's head upon his or her chest so as to relieve the strain upon the neck muscles.

For the most part, neck braces heretofore developed are custom-made to fit the neck of the wearer. Such braces are frequently heavy, expensive and uncomfortable. Furthermore, they are often difficult to ventilate so that after a period of extended use, the neck of the wearer can become wet and irritated from accumulated perspiration. In an attempt to reduce or prevent this irritation, many braces have been provided with vent holes to permit some degree of air circulation about the neck area. However, it has been found that vent holes alone frequently do not provide enough air circulation to ventilate the entire neck area and keep it dry and free from accumulated perspiration.

SUMMARY OF THE INVENTION

The present invention is directed to a new ventilated brace which can be adjustably formed into a body section encircling structure. The brace comprises one or more panels which have a plurality of vent holes to admit air into the interior of the assembled brace. These vent holes, in turn, communicate with and are connected to a network of open intersecting ventilation channels on the inside surface of the panels to conduct air throughout the interior of the brace.

OBJECTS OF THE INVENTION

It is an object of the current invention to provide a new and improved adjustable body section brace having superior interior air circulation and ventilation.

Another object of the current invention is to provide a new and improved body section brace which effectively removes heat and moisture from the interior of the brace.

Still other objects and advantages of the current invention will, in part, be obvious and will, in part, be apparent from the specification.

The invention accordingly comprises an article of manufacture possessing the features, properties and the relation of elements which will be exemplified in the article hereinafter described, and the scope of the invention will be indicated in the claims.

DETAILED DESCRIPTION OF THE INVENTION

Figure 1:
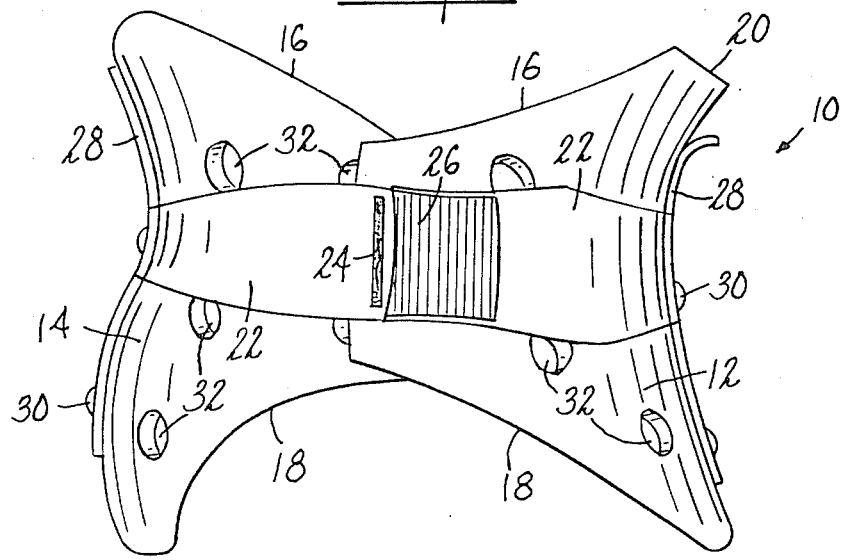
FIG. 1 is a side elevational view of a new and improved neck brace according to my invention.

Referring now to FIG. 1 of the drawing, an exemplary neck brace is generally indicated at 10. The brace 10 is preferably made of a plurality of panels, i.e., a front panel 12 and a rear panel 14. Both panels are formed from sheets of flexible material such as plastic, leather and the like.

Figure 2:
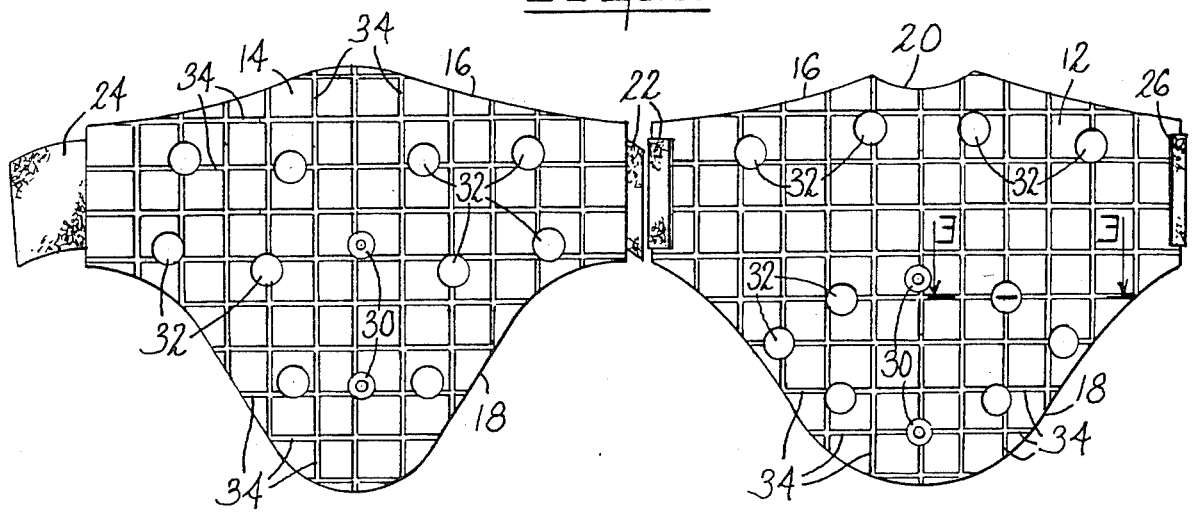
FIG. 2 is a side plan view of the panels of the neck brace of FIG. 1.

As shown in FIG. 2, both panels also have upper and lower edges, 16 and 18, respectively, which are preferably curved in shape to help fit comfortably about the wearer's neck and shoulders. When the brace is assembled, these edges generally conform to the configuration of the chin, neck, shoulders and upper chest of the wearer and substantially immobilize the wearer's head. For greater comfort, these edges may be optionally fitted with some amount of flexible padding (not shown). In a preferred embodiment, front panel upper edge, 16 is provided with a small cutout, 20 which can be located immediately under the wearer's chin to allow sufficient jaw motion for talking and eating. The panels can be of any suitable thickness but typically are about $\frac{1}{2}$" thick to provide sufficient rigidity for adequate head support.

The two panels can be secured to form a neck brace by any suitable means. It has been found to be particularly advantageous to use at least one pair of cooperating straps, 22 having mutually engaging hook and loop portions as commonly sold under the trademark Velcro, 24 and 26, respectively, attached at the ends of the straps so that the hooks of portion, 24 on one strap lock onto the loops of portion, 26 on the other strap when the two portions are pressed together. This locking action, while effectively holding the two panels together against either a direct pulling or sliding movement, permits the straps and, therefore, the panels, to be readily separated by a peeling action. By placing a plurality of hook portions on one of the straps, the placement of the mating loop portion bearing strap may be varied so that the relative amount of front panel overlap can be readily adjusted to form a neck brace which closely fits the particular wearer. The straps, 22 are held in place on both the front and rear panels by clamps, 28. These, in turn, are attached to the panels by a plurality of screws or rivets, 30. Other suitable straps and fasteners may be employed without deviating from the scope of the invention.

Figure 3:
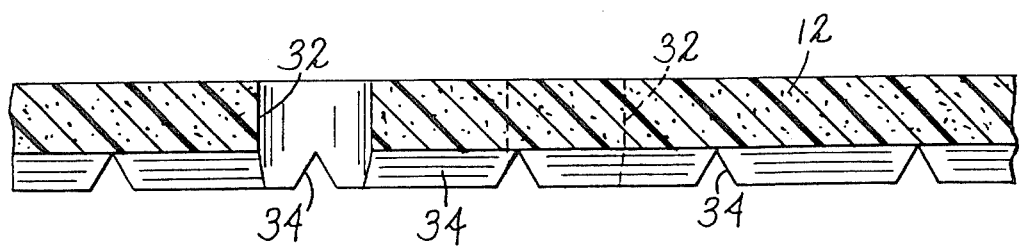
FIG. 3 is an enlarged cross sectional view taken along line 3—3 of FIG. 2.

Air circulation within the brace is accomplished by having the panels contain a plurality of vent holes, 32 as shown. To facilitate and improve the circulation of air to all parts of the neck, the present invention further includes a network of relatively shallow, interconnected ventilation channels, 34 which are inscribed, molded or machined into the inside surfaces of both panels. As shown in FIGS. 2 and 3, the vent holes, 32 preferably intersect one or more of channels, 34. This arrangement conveys a greater quantity of ventilating air over the entire neck region of the wearer as compared to a brace having only vent holes. As such, moisture and body heat are more readily absorbed and quickly conducted outside the neck brace. As a result, the wearer's neck is kept both cooler and dryer as compared to neck braces containing only vent holes.

In a preferred embodiment, the vent holes are about $\frac{1}{2}$" in diameter and the channels about $\frac{1}{8}$" deep on about a 1" square horizontally and vertically oriented grid. However, these dimensions and orientations are not critical and other hole, channel and grid dimensions, orientations and configurations may be used to accomplish such ventilation. For example, the orientation of channels, 34 can be diagonal and the grid of channels, 34 can be diamond in shape. In the preferred embodiment of the invention, the channels 34 continue to the upper and lower edges of both panels, 16 and 18.

It should be understood that neck braces within the scope of the present invention may also have additional features, such as edge padding or means for adjusting the vertical height and orientation of the individual panels. Further, the ventilation system of the current invention can be readily applied to other body section encircling, supporting and/or immobilizing structures such as back braces and leg or body casts, such applications being included within the ambit of the present disclosure.

It will thus be seen that the objects set forth above among those made apparent from the proceeding description are effectively obtained and, since certain changes may be made in the above structure without deviating from the spirit and scope of the invention, it is intended that all matter contained in the above description and shown in the accompanying drawings, shall be interpreted as illustrative and not in a limiting sense.

It is also to be understood that the following claims are intended to cover all of the generic and specific features of the invention herein described, and all statements of the scope of the invention, which, as a matter of language, might be said to fall there between.

What I claim is:

1. A body brace comprising a panel of flexible material for encircling a body section said panel having an inner surface for facing toward said body section, an opposite exterior surface for facing away from said body section and a plurality of vent holes between said inner and outer surfaces for providing air circulation to said body section, said panel inner surface having thereon a network of interconnected ventilation channels intersecting said vent holes, the width of said channels being less than the width of said vent holes.

2. The brace of claim 1 wherein each of at least a portion of said vent holes intersects a plurality of said channels.

3. The brace of claim 1 wherein said network of ventilation channels comprises a grid of horizontally and vertically oriented channels.

4. The brace of claim 3 wherein said panel comprises a single panel of flexible material.

5. The brace of claim 1 wherein said panel comprises a separate front and rear panels and means for securing and adjusting said panels to encircle said body section.

6. The brace of claim 5 wherein the means of securing and adjusting comprises at least one pair of cooperating straps having engaging hook and loop portions as commonly sold under the trademark Velcro attached to the ends of the straps enabling the straps to lock together when the Velcro portions are engaged at any point along such portions to secure the front and rear panels in place to form said body section encircling brace.

7. The brace of claim 5 wherein such brace is a neck brace.

8. The brace of claim 7 wherein the network of ventilation channels comprises a grid of horizontally and vertically oriented channels.

9. The brace of claim 7 wherein the means of securing and adjusting comprises at least one pair of cooperating straps having engaging hook and loop portions as commonly sold under the trademark Velcro attached to the ends of the straps enabling the straps to lock together when the Velcro portions are engaged to any point along such portion to secure the front and rear panels in place to form the neck brace.

10. The brace of claim 7 wherein said front and rear panels have curved upper and lower edges shaped to correspond to the configuration of the head, neck, shoulders and upper chest of the wearer when said brace is secured about said neck, said brace being adapted to cover the neck below the chin and rest upon the upper chest and shoulders of the wearer.

* * * * *